US005585104A

United States Patent [19]
Ha et al.

[11] Patent Number: 5,585,104
[45] Date of Patent: Dec. 17, 1996

[54] CLEANSING EMULSIONS

[75] Inventors: Robert B. K. Ha, Milford; Timothy J. Fowler; George E. Deckner, both of Cincinnati, all of Ohio

[73] Assignee: The Procter & Gamble Company, Cincinnati, Ohio

[21] Appl. No.: 420,390

[22] Filed: Apr. 12, 1995

[51] Int. Cl.$^6$ ............................... A61K 7/02; A61K 7/50
[52] U.S. Cl. ..................... 424/401; 514/844; 514/846
[58] Field of Search ........................ 424/401, 78.31, 424/70.16; 252/DIG. 5; 514/844, 846, 938

[56] References Cited

U.S. PATENT DOCUMENTS

| | | | |
|---|---|---|---|
| 2,798,053 | 7/1957 | Brown | 260/2.2 |
| 4,509,949 | 4/1985 | Huang et al. | 586/558 |
| 4,758,641 | 7/1988 | Hsu | 526/208 |
| 5,004,557 | 4/1991 | Nagarajan et al. | 252/174.24 |
| 5,004,598 | 4/1991 | Lochhead et al. | 424/59 |
| 5,011,681 | 4/1991 | Ciotti et al. | 424/81 |
| 5,073,371 | 12/1991 | Turner et al. | 424/401 |
| 5,073,372 | 12/1991 | Turner et al. | 424/401 |
| 5,236,710 | 8/1993 | Guerrero et al. | 424/401 |
| 5,283,009 | 2/1994 | Speckman et al. | 510/433 |
| 5,322,689 | 6/1994 | Hughes et al. | 424/401 |
| 5,344,643 | 9/1994 | Thiel et al. | 424/70.11 |
| 5,380,528 | 1/1995 | Alban et al. | 424/401 |
| 5,474,979 | 12/1995 | Ding et al. | 514/11 |
| 5,540,853 | 7/1996 | Trinh et al. | 510/101 |

FOREIGN PATENT DOCUMENTS

| | | | |
|---|---|---|---|
| 213827A2 | 3/1987 | European Pat. Off. | A61K 7/50 |
| 268164A2 | 5/1988 | European Pat. Off. | A61K 7/48 |
| 482417A1 | 4/1992 | European Pat. Off. | A61K 7/00 |

OTHER PUBLICATIONS

Carbopol®ETD 2020 Brochure, published by BF Goodrich Company, Specialty Chemicals, Cleveland, OH, Sep. 1993.

Hemker, Wil, "Universal Oil–in–Water Polyelectrolyte Emulsifiers for Advanced Cosmetic Product Formulation," Parfümerie und Kosmetik, 72. Jahrgan Nr., Nov. 1991.

Bremecker et al., "Application–triggered Drug Release from an O/W–Emulsion," Pharm. Ind. 54, Nr. 2 (1992).

Lochhead et al., "Hydrophobically Modified 'Carbopol' Resins," Soap/Cosmetics/Chemical Specialities for May, 1987.

Lochhead et al., "An Investigation of the mechanism by which hydrophobically modified hydrophilic polymers act as primary emulsifiers for oil–in–water emulsions, 1. Poly(acrylic acids) and hydroxyethyl celluloses,"Elsevier Science B.V., 1994.

Carinelli et al., "Polymer and Silicone Emulsifying Agents, How to Obtain New Emulsions with an Attractive Appearance," Cosmet. New, XVII, Mar./Apr., 1994, pp. 114–116, (Translated from Italian by the Ralph McElroy Co., Custom Divison, P.O. Box 4828, Austin, TX 78765).

Lochhead et al., "Phase Diagrams as a Formulation Guide in Aqueous Polymer/Surfactant Systems," Polymer Engineering and Science, vol. 25, No. 17, Mid–Dec., 1985.

*Primary Examiner*—Melvyn I. Marquis
*Assistant Examiner*—Robert H. Harrison
*Attorney, Agent, or Firm*—Anthony D. Sabatelli; David K. Dabbiere

[57] ABSTRACT

The present invention relates to compositions for personal cleansing in the form of oil-in-water emulsions. These emulsions have the characteristic of breaking upon contact with the skin to provide improved cleansing efficacy.

15 Claims, No Drawings

CLEANSING EMULSIONS

TECHNICAL FIELD

The present invention relates to compositions for personal cleansing in the form of oil-in-water emulsions. These emulsions are stable during storage, yet have the characteristic of de-emulsifying, that is breaking, upon contact with the skin to release the oil phase for cleansing. These compositions have the advantage of providing improved cleansing efficacy without irritating the skin or leaving the skin feeling tight or irritated.

BACKGROUND OF THE INVENTION

Personal cleansing compositions for removing dirt, oil, make-up, and like from skin are in wide use today and are marketed in a variety of forms such as creams, lotions, gels, bars, and astringents. Cold cream type cleansers are centuries old. Some of the earliest compositions were based on an animal fat or vegetable oil mixed with water and a fragrance. The fat or oil component of these early formulas was useful for removing oily debris from the skin, while the water component provided a lighter, smoother feel, and made the product easier to remove. These early compositions were unstable because the fat or oil component readily separated from the water component. These early compositions also had a short storage life because they would quickly become rancid. These early compositions were eventually improved by the addition of emulsifiers, stabilizers, antioxidants, and preservatives. Surfactants were also added to these compositions in an attempt to further improve their cleansing ability.

Cleansing compositions in the form of oil-in-water emulsions are preferred over water-in-oil emulsions because the former generally have a lighter, non-greasy, cleaner feel than the later. However, effective personal cleansing compositions are difficult to formulate as oil-in-water emulsions. An oil-in-water emulsion cleanser typically utilizes an emulsifier to keep the oil and water phases emulsified together for storage ability. This stability can actually hinder the cleansing ability of the emulsion if the oil phase is too tightly held and not released and available during the cleansing process. Furthermore, surfactants added to improve the cleansing ability of an emulsion cleanser can actually reduce cleansing ability, because the surfactant can also function as an emulsifier, thereby rendering both the surfactant and the oil phase less available for cleansing. One solution to this problem has been the development of nonemulsified two-phase cleansers. These cleansers are aesthetically unappealing, both visually and tactilely, and have the disadvantage of requiring vigorous agitation of the product prior to use.

U.S. Pat. No. 5,004,598, to Lochhead et al., issued Apr. 2, 1991, discloses mineral oil containing oil-in-water emulsions which also contain crosslinked long chain polymers, whereby the emulsion breaks upon contact with human skin. However, this document fails to teach the criticality of avoiding emulsifying surfactants, which can adversely affect the performance of a cleansing type emulsion. The compositions of the present invention comprise detersive, non-emulsifying surfactants having certain HLB requirements, as detailed below.

U.S. Pat. No. 5,011,681, to Ciotti et al, issued Apr. 30, 1991, discloses oil-in-water emulsions for removing make-up comprising a surfactant with an HLB greater than about 10, a polyalphaolefin, and a carboxylic acid copolymer containing C10–C30 substituents. However, the document does not teach that a cleansing emulsion is achievable without the polyalphaolefin. In fact, the cleansing emulsions of the present invention are achieved without relying on a polyalphaolefin and are required to be free from this component.

The compositions of the present invention utilize a carboxylic acid copolymer, as described herein, as an emulsifier. This emulsifier provides sufficient stability for storage of the product, and yet allows the product to de-emulsify or break on contact with the skin. Additionally, these compositions utilize a detersive, non-emulsifying surfactant for providing a boost in cleansing without interfering with the release of the oil phase during the cleansing process.

It is therefore an object of the present invention to provide compositions which are useful for personal cleansing.

It is another object of the present invention to provide oil-in-water emulsions which are stable and which also de-emulsify upon contact with the skin.

It is another object of the present invention to provide methods of personal cleansing.

These and other objects of this invention will become apparent in light of the following disclosure.

SUMMARY OF THE INVENTION

The present invention relates to a composition for personal cleansing in the form of an oil-in-water emulsion that is free from polymerized 1-alkenes having 10 or more carbon atoms, comprising:

(a) from about 0.01% to about 5% by weight of a copolymer comprising a monomer selected from the group consisting of acrylic acid, salts of acrylic acid, C1–C4 alkyl-substituted acrylic acid, salts of C1–C4 alkyl-substituted acrylic acid, C1–C4 alkyl esters of acrylic acid, C1–C4 alkyl esters of C1–C4 alkyl-substituted acrylic acid, maleic anhydride, and mixtures thereof; and a monomer selected from the group consisting of C10–C30 alkyl esters of acrylic acid, C10–C30 alkyl esters of C1–C4 alkyl-substituted acrylic acid, and mixtures thereof.

(b) from about 0.05% to about 20% by weight of a non-emulsifying detersive surfactant having an HLB greater than about 11, (c) from about 0.5% to about 40% by weight of an oil selected from the group consisting of mineral oil, petrolatum, C7–C40 branched chain hydrocarbons, C1–C30 alcohol esters of C1–C30 carboxylic acids, monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, propylene glycol diesters of C1–C30 carboxylic acids, C1–C30 carboxylic acid sugar esters, C1–C30 carboxylic acid sugar polyesters, polydialkylsiloxanes, polydiaryl siloxanes, polyalkarylsiloxanes, cyclomethicones having 3 to 9 silicon atoms, vegetable oils, hydrogenated vegetable oils, polypropylene glycols, polypropylene glycol C4–C20 alkyl ethers, C1–C20 carboxylic acid esters of polypropylene glycols, di-C8–C30 alkyl ethers, and mixtures thereof, and (d) from about 20% to about 99.44% by weight water.

The present invention also relates to methods of personal cleansing utilizing these compositions.

All percentages and ratios used herein are by weight of the total composition and all measurements made are at 25° C. or room temperature, unless otherwise designated. All weight percentages, unless otherwise indicated, are on an actives weight basis. The invention hereof can comprise, consist of, or consist essentially of, the essential as well as the optional ingredients and additional components described herein.

DETAILED DESCRIPTION OF THE INVENTION

The oil-in-water emulsion compositions of the present invention are useful for personal cleansing, particularly of the face and neck areas.

These compositions de-emulsify when placed in contact with the skin, which is to say that they break or separate. Without being limited by theory, it is believed that the electrolytes present on the skin interact with the carboxylic acid copolymer, thereby causing the emulsion to de-emulsify, thereby freeing the oil phase to dissolve and aid in cleansing oily debris from the skin. Also, because these emulsions contain a nonemulsifying detersive surfactant component, additional cleansing power is also obtained therefrom.

The compositions of the present invention are free from polymerized 1-alkenes having 10 or more carbon atoms, which means that these compositions do not contain appreciable amounts of these materials, i.e. not more than about 1%. Polymerized 1-alkenes having 10 or more carbon atoms are polymers of alkenes such as 1-decene, 1-undecene, 1-dodecane, 1-tridecane, and the like. An example of such a material is poly(1-decene).

The emulsion compositions of the present invention can be in the form of "rinse-off" compositions as distinguished from "leave-on" or "water-less" cleansers. By "rinse-off" is meant that these compositions are used in a cleansing process whereby the compositions is ultimately rinsed or washed from the skin with water to complete the cleansing process. The emulsion compositions can also be in the form of "wipe-off" compositions which are distinguished from "leave-on" compositions. These "wipe-off" compositions are typically removed by wiping with a device such as a cotton ball, a cotton pad, a tissue, or a towel, and the like.

The term "pharmaceutically-acceptable," as used herein, means that the compositions, topical carriers, and components thereof so described are of sufficiently high purity and are suitable for use in contact with human skin without undue toxicity, incompatibility, instability, allergic response, and the like.

The term "physical stability," as used herein, means that the compositions of the present invention exhibit physical characteristics such as retention of viscosity and resistance to phase separation. For example, the compositions of the present invention typically maintain their physical stability for at least 3 months at 40° C.

Copolymer

The compositions of the present invention comprise from about 0.01% to about 5%, preferably from about 0.05% to about 0.75% and more preferably from about 0.10% to about 0.50% of a copolymer comprising a first monomer and a second monomer, wherein the first monomer is selected from the group consisting of acrylic acid, salts of acrylic acid, C1–C4 alkyl-substituted acrylic acid, salts of C1–C4 alkyl-substituted acrylic acid, C1–C4 alkyl esters of acrylic acid, C1–C4 alkyl esters of C1–C4 alkyl-substituted acrylic acid, maleic anhydride, and mixtures thereof; and the monomer is a long chain ester monomer selected from the group consisting of C10–C30 alkyl esters of acrylic acid, C10–C30 alkyl esters of C1–C4 alkyl-substituted acrylic acid, and mixtures thereof. The salts of the acids described in the previous sentence are selected from the group consisting of alkali metal salts, alkaline metal salts, ammonium salts, and mono-, di-, tri-, and tetra-alkyl ammonium salts. The C1–C4 alkyl-substituted acrylic acids described in the first sentence of this paragraph include methacrylic acids, ethacrylic acids, and the like, wherein the alkyl substituent can be either on the C2 or C3 position of the acid molecule. The C1–C4 alkyl esters described in the first sentence in this paragraph include methyl and ethyl esters as well as branched C3 and C4 esters.

Preferably these copolymers are crosslinked and further comprise a crosslinking agent that is a polyalkenyl polyether of a polyhydric alcohol containing more than one alkenyl ether group per molecule, wherein the parent polyhydric alcohol contains at least 3 carbon atoms and at least 3 hydroxyl groups. Preferred crosslinking agents are those selected from the group consisting of allyl ethers of sucrose and allyl ethers of pentaerythritol, and mixtures thereof. These polymers useful in the present invention are more fully described in U.S. Pat. No. 5,087,445, to Haffey et al., issued Feb. 11, 1992; U.S. Pat. No. 4,509,949, to Huang et al., issued Apr. 5, 1985, U.S. Pat. No. 2,798,053, to Brown, issued Jul. 2, 1957; which are incorporated by reference herein in their entirety. See also, *CTFA International Cosmetic Ingredient Dictionary*, fourth edition, 1991, pp. 12 and 80; which is also incorporated herein by reference in its entirety.

Examples of commercially available copolymers useful herein include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytritol. These copolymers are known as acrylates/C10–30 alkyl acrylate crosspolymers and are commercially available as Carbopol® 1342, Pemulen TR-1, and Pemulen TR-2, from B. F. Goodrich.

The polymers are prepared, for example, by polymerizing a preponderant amount of a carboxylic acid monomer and a lesser amount of a long chain acrylate ester monomer. Amounts of the carboxylic monomer can be in the range of 50 to 99% by weight, preferably 80 to 99% by weight, and especially 90 to 99% by weight whereas amounts of the acrylate ester can be in the range of 1 to 50% by weight, preferably 1 to 20% by weight, especially 2 to 10% by weight. Amounts of the carboxylic monomer and the long chain acrylate ester are based on the combined weight of both components. It should be understood that more than one carboxylic monomer and more than one long chain acrylate ester can be used.

The polymers can also be crosslinked by inclusion of a suitable crosslinking agent in amounts of about 0.1 to 4%, preferably 0.2 to 1% by weight based on the combined weight of the carboxylic monomer and the acrylate ester.

Production of the copolymers of this invention employs a monomeric mixture which contains two essential monomeric ingredients, each in certain proportions, one being a monomeric carboxylic monomer and the other being an acrylic ester having a long chain aliphatic group. Optionally, there is included in the monomeric mixture a crosslinking agent.

The copolymers of a carboxylic monomer and an acrylic ester having a long chain aliphatic group can have polymerized therein a major proportion of a lower C1–C4 alkyl ester of acrylic acid, methacrylic acid, or ethacrylic acid, in amounts of 0–40% by weight, preferably 5–30%, based on the total monomer.

The carboxylic monomers useful in the production of the copolymers of this invention are the olefinically-unsaturated carboxylic acids containing at least one activated carbon-to-carbon olefinic double bond, and at least one carboxyl group, that is, an acid containing an olefinic double bond which readily functions in polymerization because of its presence in the monomer molecule either in the alpha-beta position with respect to a carboxyl group or as part of a terminal methylene grouping. The anhydrides can also be used, especially maleic anhydride.

The preferred carboxylic monomers for use in this invention are the monoolefinic acrylic acids having the general structure

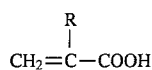

wherein R is a substituent selected from the group consisting of hydrogen, halogen, hydroxyl, lactone, lactam, and the cyano (—C≡N) group, monovalent alkyl radicals, monovalent aryl radicals, monovalent aralkyl radicals, monovalent alkaryl radicals and monovalent cycloaliphatic radicals. Of this class, acrylic acid itself is most preferred because of its generally lower cost, ready availability, and ability to form superior polymers. Another particularly preferred carboxylic monomer is maleic anhydride.

The preferred acrylic ester monomers having long chain aliphatic groups are derivatives of acrylic acid represented by the formula:

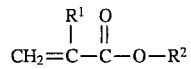

wherein $R^1$ is selected from the group consisting of hydrogen, methyl and ethyl groups and $R^2$ is selected from the group consisting of alkyl groups having from 8 to 30 carbon atoms and oxyalkylene and carbonyloxyalkylene groups, preferably alkyl groups of 10 to 30 carbon atoms, more preferably alkyl groups of 10 to 22 carbon atoms. The oxyalkylene and carbonyloxyalkylene groups are particularly oxyethylene and carboxyloxyethylene groups. Representative higher alkyl acrylic esters are decyl acrylate, lauryl acrylate, stearyl acrylate, behenyl acrylate and meliesyl acrylate, and the corresponding methacrylates.

The copolymers described herein, when tested in the form of 0.2% aqueous mucilages, have a viscosity of 100 to 50,000 cps, preferably 250 to 40,000 cps, and especially 500 to 35,000 cps. In the form of 1.0% aqueous mucilages, have a viscosity of 1,000 to 100,000 cps, preferably 2,000 to 90,000 cps, and especially 2,500 to 85,000 cps. These viscosities are measured to about 25° C. using a Brookfield RVT model viscometer at a spindle speed of 20 rpm in the pH range of 7.2 to 7.6. The viscosity of these mucilages is an indication of the molecular weight of the herein-disclosed modified polymers which are characterized as being lightly crosslinked.

The preferred crosslinking agent, if one is employed, is a polyalkenyl polyether having more than one alkenyl ether grouping per molecule. The most useful possess alkenyl groups in which an olefinic double bond is present, attached to a terminal methylene grouping, $CH_2=C<$. They are made by the etherification of a polyhydric alcohol containing at least 4 carbon atoms and at least 3 hydroxyl groups. Compounds of this class may be produced by reacting an alkenyl halide, such as allyl chloride or allyl bromide with a strongly alkaline aqueous solution of one or more polyhydric alcohols. The product is a complex mixture of polyethers with varying numbers of ether groups. Analysis reveals only the average number of ether groupings on each molecule. Efficiency of the polyether crosslinking agent increases with the number of potentially polymerizable groups on the molecule. It is preferred to utilize polyethers containing an average of two or more alkenyl ether groupings per molecule.

The copolymers are preferably made by polymerization in an inert diluent having some solubilizing action on one or more of the monomeric ingredients but substantially none on the resultant polymer. Polymerization in mass may be employed but is not preferred because of the difficulty in working up the solid polymeric masses obtained. Polymerization in an aqueous medium containing a water-soluble free radical catalyst peroxygen is useful, the product being obtained either as a granular precipitate or as a highly swollen gel, either of which may be used directly or which are easily further subdivided and dried.

Polymerization in an organic liquid which is a solvent for the monomers but a non-solvent for the polymer, or in a mixture of such solvents, in the presence of a solvent-soluble catalyst, is most preferred because the product is usually obtained as a very fine, friable and often fluffy precipitate which, after solvent removal, seldom requires grinding or other treatment before use. Suitable solvents for the latter method include benzene, xylene, tetralin, hexane, heptane, carbon tetrachloride, methyl chloride, ethyl chloride, bromo trichloro methane, ethyl acetate, dimethyl carbonate, diethyl carbonate, ethylene dichloride, and mixtures of these and other solvents.

Polymerization can also be carried out in an aqueous medium of soluble nonredox multivalent inorganic salt. The acid is too soluble in plain water, therefore, the inorganic salt is added to insolubilize the acid. In this manner, another phase is introduced and the acid is polymerized in a suspension rather than in solution.

The aqueous medium can be a concentrated solution of the salt or it can be a salt slurry of the salt. The difference between the two is considerable. Whereas a concentrated solution of magnesium sulfate salt at a reaction temperature is composed of about 2.5 weight parts of the salt per single weight part of water, a slurry of the salt is composed of about 20 weight parts of the salt per single weight part of water. The use of a concentrated salt solution as the reaction medium is preferred.

Although magnesium sulfate is the preferred salt, other organic salts or hydrates thereof can be used, including the nonredox multivalent ion salts such as potassium sulfate, calcium chloride, secondary sodium phosphate and salts employing combinations of anions and cations such as aluminum, barium, beryllium, cadmium, calcium, chloride, chromium, cobalt, lead, magnesium, manganese, molybdate, nickel, selenate, strontium, sulfate, tin, tungsten, zinc, and the like.

Success of this polymerization method depends on the fact that the polymerization reaction takes place in discrete and separate oil-in-water droplets. Therefore, water solubility of the inorganic salt employed should be at least about one-half molar in order to salt out the monomer and the formed water-soluble polymer. Moreover, the readily soluble salts can be readily washed out of the finished polymer.

Polymerization in the diluent medium is carried out in the presence of a free radical catalyst in a closed vessel in an inert atmosphere and under autogenous pressure or artificially-induced pressure or in an open vessel under reflux at atmospheric pressure. The temperature of the polymerization may be varied from 0° to 100° C., depending to a large degree on the molecular weight desired in the polymer. Polymerization under reflux at 50° to 90° C., under atmospheric pressure using a free radical catalyst is generally effective in bringing a polymer yield of 75% to 100% in less than 10 hours.

Suitable polymerization catalysts include peroxygen compounds such as sodium potassium and ammonium persulfates, caprylyl peroxide, benzoyl peroxide, hydrogen peroxide, pelargonyl peroxide, cumene hydroperoxides, tertiary butyl diperphthalate, tertiary butyl perbenzoate, sodium peracetate, sodium percarbonate, and the like, as well as azo diisobutyryl nitrile, hereinafter referred to as azoisobutyronitrile. Other catalysts utilizable are the so-called "re-dox" type of catalysts and the heavy-metal activated catalyst systems.

The copolymers generally do not attain their maximum properties in water until converted to a partial alkali, ammonium or amine salt. The neutralizing agent is preferably a monovalent alkali such as sodium, potassium, lithium or ammonium hydroxide, sodium, potassium, lithium, or ammonium carbonate, sodium, potassium, lithium, or ammonium bicarbonate, or mixtures thereof and also amine bases having not more than one primary or secondary amino group, for example, ethanolamine, diethanolamine, triethanolamine, trimethyl amine, and the like.

Conventional oil-in-water emulsions have particle size of less than 10 microns, preferably 0.1–5 microns. Surprisingly, the oil-in-water emulsions prepared herein with these copolymers having a much larger particle size averaging about 50 microns and are in the range of about 10 to about 100 microns.

The copolymers, which can contain a small proportion of long chain acrylate esters, can function as primary emulsifiers, whereas polymers similar to the modified polymers but devoid of long chain acrylate esters do not possess this property. The emulsions also de-emulsify when contacted with the.

See, also, U.S. Pat. No. 5,004,598, to Lochhead et al., issued Apr. 2, 1991, which is incorporated by reference herein in its entirety.

Nonemulsifying Detersive Surfactant

The compositions of the present invention comprise from about 0.05% to about 20%, preferably from about 0.10% to about 15%, and more preferably from about 0.5% to about 10% of a nonemulsifying, detersive surfactant selected from the group consisting of nonionic surfactants, anionic surfactants, cationic surfactants, amphoteric surfactants, zwitterionic surfactants, and mixtures thereof. Such nonemulsifying detersive surfactants are well-known to those skilled in the art. By "nonemulsifying" is meant that these surfactants do not appreciably emulsify the water and oil components of a composition to form an emulsion containing a phase of dispersed particles in a continuous phase. By "detersive" is meant that these surfactants provide a cleansing or detergent benefit. Surfactants having relatively high HLB values are preferred herein, because of their reduced ability to act as emulsifiers. In the present invention, a single surfactant or a mixture of surfactants can be utilized. The HLB of the single surfactant and the weighted average HLB for a mixture of surfactants should be greater than about 11, preferably from about 11 to about 18, and more preferably from about 12 to about 17. The term "HLB" is well-known to those skilled in the art and stands for "hydrophilic-lipophilic balance" and is further described in *The HLB System. A Time-saving Guide to Emulsifier Selection* (published by ICI Americas Inc., Wilmington, Del., 1984), which is incorporated by reference herein in its entirety. Also, the preferred surfactants useful herein generally do not contain alkyl substituents having about 15 carbon atoms or more, although such materials can be used if the overall HLB value of the surfactant component is appropriately adjusted.

Nonlimiting examples of suitable surfactants for use in the compositions of the present invention are disclosed in McCutcheon's, *Detergents and Emulsifiers*, North American edition (1986), published by allured Publishing Corporation; McCutcheon's, *Functional Materials*, North American Edition (1992); U.S. Pat. No. 5,151,210, to Steuri et al., issued Sep. 29, 1992; U.S. Pat. No. 5,151,209, to McCall et al., issued Sep. 29, 1992; U.S. Pat. No. 5,120,532, to Wells et al., issued Jun. 9, 1992; U.S. Pat. No. 5,011,681, to Ciotti et al., issued Apr. 30, 1991; U.S. Pat. No. 4,788,006, to Bolich, Jr. et al., issued Nov. 29, 1988; U.S. Pat. No. 4,741,855, to Grote et al, issued May 3, 1988; U.S. Pat. No. 4,704,272, to Oh et al, issued Nov. 3, 1987; U.S. Pat. No. 4,557,853, to Collins, issued Dec. 10, 1985; U.S. Pat. No. 4,421,769, to Dixon et al., issued Dec. 20, 1983; and U.S. Pat. No. 3,755,560, to Dickert et al., issued Aug. 28, 1973; each of these documents being incorporated herein by reference in its entirety.

The following are nonlimiting examples of surfactants useful herein. It should be recognized that care should be taken in selecting surfactant materials such that the overall HLB requirements of the invention are met.

Among the nonionic surfactants that are useful herein are those that can be broadly defined as condensation products of long chain alcohols, e.g. C8–30 alcohols, with sugar or starch polymers, i.e., glycosides. These compounds can be represented by the formula $(S)_n$—O—R wherein S is a sugar moiety such as glucose, fructose, mannose, and galactose; n is an integer of from about 1 to about 1000, and R is a C8–30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8–20 alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel).

Other useful nonionic surfactants include the condensation products of alkylene oxides with fatty acids (i.e. alkylene oxide esters of fatty acids). When these particular anionic are used, it is preferably to use them at low concentrations, preferably in combination with one or more of the other surfactants disclosed herein. These materials have the general formula $RCO(X)_nOH$ wherein R is a C10–30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 1 to about 100. Other nonionic surfactants are the condensation products of alkylene oxides with 2 moles of fatty acids (i.e. alkylene oxide diesters of fatty acids). These materials have the general formula $RCO(X)_nOOCR$ wherein R is a C10–30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 1 to about 100. Other nonionic surfactants are the condensation products of alkylene oxides with fatty alcohols (i.e. alkylene oxide ethers of fatty alcohols). These materials have the general formula $R(X)_nOR'$ wherein R is a C10–30 alkyl group, X is —$OCH_2CH_2$— (i.e. derived from ethylene glycol or oxide) or —$OCH_2CHCH_3$— (i.e. derived from propylene glycol or oxide), and n is an integer from about 1 to about 100 and R' is H or a C10–30 alkyl group. Still other nonionic surfactants are the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. These materials have the general formula $RCO(X)_nOR'$ wherein R and R' are C10–30 alkyl groups, X is —$OCH_2CH_2$ (i.e. derived from ethylene glycol or oxide) or —$OCH_2CHCH_3$— (derived from propylene glycol or oxide), and n is an integer from about 1 to about 100. Nonlimiting examples of these alkylene oxide derived nonionic surfactants include ceteth-1, ceteth-2, ceteth-6, ceteth-10, ceteth-12, ceteareth-2, ceteareth-6, ceteareth-10, ceteareth-12, steareth-1, steareth-2, steareth-6, steareth-10, steareth-12, PEG-2 stearate, PEG-4 stearate, PEG-6 stearate, PEG-10 stearate, PEG-12 stearate, PEG-20 glyceryl stearate, PEG-80 glyceryl tallowate, PPG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants corresponding to the structural formula:

wherein: $R^1$ is H, $C_1$–$C_4$ alkyl, 2-hydroxyethyl, 2-hydroxypropyl, preferably $C_1$–$C_4$ alkyl, more preferably methyl or ethyl, most preferably methyl; $R^2$ is $C_5$–$C_{31}$ alkyl or alkenyl, preferably $C_7$–$C_{19}$ alkyl or alkenyl, more preferably $C_9$–$C_{17}$ alkyl or alkenyl, most preferably $C_{11}$–$C_{15}$ alkyl or alkenyl; and Z is a polhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R^2CO$— moiety is derived from coconut oil fatty acids). Processes for making compositions containing polyhydroxy fatty acid amides are disclosed, for example, in G.B. Patent Specification 809, 060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934; which are incorporated herein by reference in their entirety.

A wide variety of anionic surfactants are useful herein. See, e.g., U.S. Pat. No. 3,929,678, to Laughlin et al., issued Dec. 30, 1975, which is incorporated herein by reference in its entirety. Nonlimiting examples of anionic surfactants include the alkoyl isethionates, and the alkyl and alkyl ether sulfates. The alkoyl isethionates typically have the formula $RCO$—$OCH_2CH_2SO_3M$ wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from the group consisting of ammonium cocoyl isethionate, sodium cocoyl isethionate, sodium lauroyl isethionate, sodium stearoyl isethionate, and mixtures thereof.

The alkyl and alkyl ether sulfates typically have the respective formulae $ROSO_3M$ and $RO(C_2H_4O)_xSO_3M$, wherein R is alkyl or alkenyl of from about 10 to about 30 carbon atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

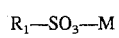

wherein $R_1$ is chosen from the group consisting of a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and b-alkyloxy alkane sulfonates. Examples of these materials are sodium lauryl sulfate and ammonium lauryl sulfate.

Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, caster oil, tallow, lard, etc.) The fatty acids can also be synthetically prepared. Soaps are described in more detail in U.S. Pat. No. 4,557,853, cited above.

Cationic surfactants can also be utilized in the present invention, however, care should be taken to avoid their complexation with the copolymer of the present invention. This undesired complexation can be avoided by first neutralizing the copolymer with a suitable base before the cationic surfactant is added to the compositions. Nonlimiting examples of cationic surfactants useful herein include cationic ammonium salts such as those having the formula:

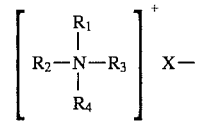

wherein $R_1$, is selected from an alkyl group having from about 12 to about 22 carbon atoms, or aromatic, aryl or alkaryl groups having from about 12 to about 22 carbon atoms, $R_2$, $R_3$, and $R_4$ are independently selected from hydrogen, an alkyl group having from about 1 to about 22 carbon atoms, or aromatic, aryl or alkaryl groups having from about 12 to about 22 carbon toms; and X is an anion selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups can also contain ether linkages, or hydroxy or amino group substituents (e.g., the alkyl groups can contain polyethylene glycol and polypropylene glycol moieties).

More preferably, $R_1$ is an alkyl group having from about 12 to about 22 carbon atoms; $R_2$ is selected from H or an alkyl group having from about 1 to about 22 carbon atoms; $R_3$ and $R_4$ are independently selected from H or an alkyl group having from about 1 to about 3 carbon atoms; and X is as described in the previous paragraph.

Most preferably, $R_1$ is an alkyl group having from about 12 to about 22 carbon atoms; $R_2$, $R_3$, and $R_4$ are selected from H or an alkyl group having from about 1 to about 3 carbon atoms; and X is as described previously.

Alternatively, other useful cationic surfactants include amino-amides, wherein in the above structure $R_1$ is alternatively $R_5CO-(CH_2)_n-$, wherein $R_5$ is an alkyl group having from about 12 to about 22 carbon atoms, and n is an integer from about 2 to about 6, more preferably from about 2 to about 4, and most preferably from about 2 to about 3. Nonlimiting examples of these cationic emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl dimethyl ammonium chloride, distearyl methyl ammonium bromide, and mixtures thereof. Additional quaternary ammonium salts include those wherein the C12 to C22 alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the C16 to C18 range. The term "coconut" refers to an alkyl group derived from a coconut fatty acid, which generally have mixtures of alkyl chains in the C12 to C14 range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$–$C_{18}$) and one contains an anionic water solubilizing group, e.g., carboxy, sulfonate, sulfate, phosphate, or phosphonate. Examples are alkyl imino acetates, and iminodialkanoates and aminoalkanoates of the formulas $RN[CH_2)_mCO_2M]_2$ and $RNH(CH_2)_mCO_2M$ wherein m is from 1 to 4, R is a $C_8$–$C_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072 which is incorporated herein by reference in its entirety; N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in is entirety. Other examples of useful amphoterics include phosphates, such as coamidopropyl PG-dimonium chloride phosphate (commercially available as Monaquat PTC, from Mona Corp.).

Also useful herein as amphoteric or zwitterionic surfactants are the betaines. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxypropyl) carboxymethyl betaine, oleyl dimethyl gamma-carboxypropyl betaine lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Other useful amphoteric and zwitterionic surfactants include the sultaines and hydroxysultaines such as cocamidopropyl hydroxysultaine (available as Mirataine CBS from Rhone-Poulenc), and the alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

Nonlimiting examples of preferred surfactants for use herein are those selected from the group consisting of C8–C14 glucose amides, C8–C14 alkyl polyglucosides, sodium lauryl sulfate, sodium lauryl sarcosinate, sodium laureth sulfate, ammonium lauryl sulfate, ammonium laureth sulfate, dilauryl dimethyl ammonium chloride, dimyristyl dimethyl ammonium chloride, sodium lauryl taurate, lauryl betaine, lauramide MEA (also known as monoethanoamide of lauric acid), lauramide DEA (also known as diethanolamide of lauric acid), PEG-8 dilaurate, lauryl dimethyl carboxymethyl betaine, sodium lauryl soap, sodium tallow soap, laureth-3, laureth-10, laureth-20, PEG-6 dilaurate, sodium deceth sulfate, sodium myreth sulfate, lauroyl sarcosine, myristyl betaine, and mixtures thereof.

Oil

The compositions of the present invention comprise from about 0.5% to about 40%, preferably from about 1% to about 25%, and more preferably from about 2% to about 15% of an oil selected from the group consisting of mineral oil, petrolatum, C7–C40 branched chain hydrocarbons, C1–C30 alcohol esters of C1–C30 carboxylic acids, C1–C30 alcohol esters of C2–C30 dicarboxylic acids, monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, propylene glycol diesters of C1–C30 carboxylic acids, C1–C30 carboxylic acid monoesters and polyesters of sugars, polydialkylsiloxanes, polydiarylsiloxanes, polyalkarylsiloxanes, cyclomethicones having 3 to 9 silicon atoms, vegetable oils, hydrogenated vegetable oils, polypropylene glycols, polypropylene glycol C4–C20 alkyl ethers, di C8–C30 alkyl ethers, and mixtures thereof. As described above, the compositions are free from polymerized 1-alkenes having 10 or more carbon atoms.

The oil materials generally having low solubility in water, generally less than about 1% by weight at 25° C. Nonlimiting examples of suitable oil components include, but are not limited to, the following materials. Some of these materials are further described in U.S. Pat. No. 4,919,934, to Deckner et al., issued Apr. 24, 1990, which is incorporated herein by reference in its entirety.

Mineral oil, which is also known as petrolatum liquid, is a mixture of liquid hydrocarbons obtained from petroleum. See The Merck Index, Tenth Edition, Entry 7048, p. 1033 (1983) and International Cosmetic Ingredient Dictionary, Fifth Edition, vol. 1, p. 415–417 (1993), which are incorporated by reference herein in their entirety.

Petrolatum, which is also known as petroleum jelly, is a colloidal system of nonstraight-chain solid hydrocarbons and high-boiling liquid hydrocarbons, in which most of the liquid hydrocarbons are held inside the micelles. See The Merck Index, Tenth Edition, Entry 7047, p. 1033 (1983); Schindler, *Drug. Cosmet. Inc.*, 89, 36–37, 76, 78–80, 82 (1961); and International Cosmetic Ingredient Dictionary, Fifth Edition, vol. 1, p. 537 (1993), which are incorporated by reference herein in their entirety.

Straight and branched chain hydrocarbons having from about 7 to about 40 carbon atoms are useful herein. Nonlimiting examples of these hydrocarbon materials include dodecane, isododecane, squalane, cholesterol, hydrogenated polyisobutylene, docosane (i.e. a $C_{22}$ hydrocarbon), hexadecane, isohexadecane (a commercially available hydrocarbon sold as Permethyl® 101A by Presperse, South Plainfield, N.J.). Also useful are the C7–C40 isoparaffins, which are C7–C40 branched hydrocarbons.

Useful oils include C1–C30 alcohol esters of C1–C30 carboxylic acids and of C2–C30 dicarboxylic acids, including straight and branched chain materials as well as aromatic derivatives. Also useful are esters such as monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, and propylene glycol diesters of C1–C30 carboxylic acids. Straight chain, branched chain and aryl carboxylic acids are included herein. Also useful are propoxylated and ethoxylated derivatives of these materials. Nonlimiting examples include diisopropyl sebacate, diisopropyl adipate, isopropyl myristate, isopropyl palmitate, myristyl propionate, ethylene glycol distearate, 2-ethylhexyl palmitate, isodecyl neopentanoate, $C_{12-15}$ alcohols benzoate, di-2-ethylhexyl maleate, cetyl palmitate, myristyl myristate, stearyl stearate, cetyl stearate, behenyl behenrate, dioctyl maleate, dioctyl sebacate, diisopropyl adipate, cetyl octanoate, diisopropyl dilinoleate, caprilic/capric triglyceride, PEG-6 caprylic/capric triglyceride, PEG-8 caprylic/capric triglyceride, and mixtures thereof.

Also useful are various C1–C30 monoesters and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7–8, and in which the fatty acid moieties are C18 mono- and/or di-unsaturated and behenic, in a molar ratio of unsaturates:behenic of 1:7 to 3:5. A particularly preferred solid sugar polyester is the octaester of sucrose in which there are about 7 behenic fatty acid moieties and about 1 oleic acid moiety in the molecule. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

Silicones such as polydialkylsiloxanes, polydiarylsiloxanes, polyalkarylsiloxanes, and cyclomethicones having 3 to 9 silicon atoms are useful oils. These silicones include both volatile and nonvolatile materials. These silicones are disclosed in U.S. Pat. No. 5,069,897, to Orr, issued Dec. 3, 1991, which is incorporated by reference herein in its entirety. The polyalkylsiloxanes include, for example, polyalkylsiloxanes with viscosities of from about 0.5 to about 100,000 centistokes at 25° C. Such polyalkylsiloxanes correspond to the general chemical formula $R_3SiO[R_2SiO]_xSiR_3$ wherein R is an alkyl group (preferably R is methyl or ethyl, more preferably methyl) and x is an integer from 0 to about 500, chosen to achieve the desired molecular weight. Commercially available polyalkylsiloxanes include the polydimethylsiloxanes, which are also known as dimethicones, nonlimiting examples of which include the Vicasil® series sold by General Electric Company and the Dow Corning® 200 series sold by Dow Corning Corporation. Specific examples of polydimethylsiloxanes useful as emollients herein include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Cyclic polyalkylsiloxanes useful herein include those corresponding to the general chemical formula $[SiR_2—O]_n$ wherein R is an alkyl group (preferably R is methyl or ethyl, more preferably methyl) and n is an integer from about 3 to about 9, more preferably n is an integer from about 3 to about 7, and most preferably n is an integer from about 4 to about 6. When R is methyl, these materials are typically referred to as cyclomethicones. Commercially available cyclomethicones include Dow Corning® 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains the cyclomethicone pentamer (i.e. n=5), and Dow Corning® 245 fluid having a viscosity of 4.2 centistokes and a boiling point of 205° C., which primarily contains a mixture of the cyclomethicone tetramer and pentamer (i.e. n=4 and 5), and Dow Corning® 345 fluid having a viscosity of 4.5 centistokes and a boiling point of 217°, which primarily contains a mixture of the cyclomethicone tetramer, pentamer, and hexamer (i.e. n=4, 5, and 6). Also useful are materials such as trimethylsiloxysilicate, which is a polymeric material corresponding to the general chemical formula $[(CH_2)_3SiO_{1/2}]_x[SiO_2]_y$, wherein x is an integer from about 1 to about 500 and y is an integer from about 1 to about 500. A commercially available trimethylsiloxysilicate is sold as a mixture with dimethicone as Dow Corning® 593 fluid. Also useful herein are dimethiconols, which are hydroxy terminated dimethyl silicones. These materials can be represented by the general chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer from 0 to about 500, chosen to achieve the desired molecular weight. Commercially available dimethiconols are typically sold as mixtures with dimethicone or cyclomethicone (e.g. Dow Corning® 1401, 1402, and 1403 fluids). Also useful herein are polyalkylaryl siloxanes, with polymethylphenyl siloxanes having viscosities from about 15 to about 65 centistokes at 25° C. being preferred. These materials are available, for example, as SF 1075 methylphenyl fluid (sold by General Electric Company) and 556 Cosmetic Grade phenyl trimethicone fluid (sold by Dow Corning Corporation).

Vegetable oils and hydrogenated vegetable oils are also useful herein. Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, and mixtures thereof.

Also useful are polypropylene glycols, C4–C20 alkyl ethers of polypropylene glycols, C1–C20 carboxylic acid esters of polypropylene glycols, and di-C8–C30 alkyl ethers. Nonlimiting examples of these materials include PPG-14 butyl ether, PPG-15 stearyl ether, PPG-9, PPG-12, PPG-15, PPG-17, PPG-20, PPG-26, PPG-30, PPG-34, dioctyl ether, dodecyl octyl ether, and mixtures thereof.

Water

The compositions of the present invention comprise from about 20% to about 99.44%, more preferably from about 50% to about 95%, and most preferably from about 70% to about 90% of water. The exact level of water will depend upon the form of the product and the desired moisture content.

Additional Components

The compositions of the present invention can comprise a wide range of additional components. However, care should be taken to avoid adding components which can prematurely cause the emulsion to break during storage. The *CTFA Cosmetic Ingredient Handbook*, Second Edition, 1992, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these functional classes include: absorbents, abrasives, anti-acne agents, anticaking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, and suspending agents), suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include solubilizing agents, sequestrants, and keratolytics, and the like. Low levels of emulsifying surfactants can also be used herein, provided they are added in such a manner to avoid over-emulsification of the formulation and as long as the fast-breaking or de-emulsifying properties of the compositions are not effected Nonlimiting examples of these additional components cited in the *CFTA Cosmetic Ingredient Handbook*, as well as other materials useful herein, include the following: vitamins and derivatives thereof [e.g., vitamin C, Vitamin A (i.e. retinoic acid), retinol, retinoids, and the like]; sunscreening agents; other silicone materials such as dimethiconol, dimethicone copolyol, and amodimethicone, and the like); antioxidants; anti-microbial agents; preservatives; emulsifiers; polyethylene glycols and polypropyleneglycols; polymers for aiding the film-forming properties and substantivity of the composition (such as a copolymer of eicosene and vinyl pyrrolidone, an example of which is available from GAF Chemical Corporation as Ganex® V-220); preservatives for maintaining the antimicrobial integrity of the compositions; anti-acne medicaments (e.g., resorcinol, sulfur, salicyclic acid, erythromycin, zinc, and the like); skin bleaching (or lightening) agents including but not limited to hydroquinone, kojic acid; antioxidants; chelators and sequestrants; thickening agents such as carbomers (homopolymers of acrylic acid crosslinked with an allyl ether of pentaerythritol or an allyl ether of sucrose), crosslinked and noncrosslinked nonionic and cationic polyacrylamides [e.g., Salcare® SC92 which has the CTFA designation polyquaternium 32 (and) mineral oil, and Salcare® SC 95 which has the CTFA designation polyquaternium 37 (and) mineral oil (and) PPG-1 trideceth-6, and the nonionic Seppi-Gel polyacrylamides available from Seppic Corp.]; aesthetic components such as fragrances, pigments, colorings, essential oils, skin senates, astringents, skin soothing agents, skin healing agents and the like, [nonlimiting examples of these aesthetic components include clove oil, menthol, camphor, eucalyptus oil, eugenol, menthyl lactate, witch hazel distillate, bisabolol, dipotassium glycyrrhizinate and the like]; and skin conditioning agents such as urea and glycerol, and also the propoxylated glycerols described in U.S. Pat. No. 4,976,953, to Orr et al., issued Dec. 11, 1990, which is incorporated by reference herein in its entirety.

Some of these additional ingredients are described in more detail below.

Sunscreen Agents

The compositions of the present invention can also comprise one or more sunscreen agents. When a sunscreen agent is employed, it is found that the compositions of the present invention are also useful for protecting human skin from the harmful effects of ultraviolet radiation.

The sunscreen agent can comprise from about 0.1% to about 30%, more preferably from about 0.5% to about 25%, and most preferably from about 1% to about 20% of the composition. Exact amounts of sunscreen agent will vary depending upon the sunscreen or sunscreens chosen and the desired Sun Protection Factor (SPF) to be achieved. SPF is a commonly used measure of photoprotection of a sunscreen against erythema. The SPF is defined as the ratio of the ultraviolet energy required to produce minimal erythema on protected skin to that required to produce the same minimal erythema on unprotected skin in the same individual. See Federal Register, Vol. 43, No. 166, pp. 38206–38269, Aug. 25, 1978, which is incorporated herein by reference in its entirety.

A wide variety of sunscreen agents are useful herein. These sunscreen agents include both organic compounds and their salts as well as inorganic particulate materials. Without being limited by theory, it is believed that sunscreen agents provide protection from ultraviolet radiation by one or more of the following mechanisms including absorption, scattering, and reflection of the ultraviolet radiation. Nonlimiting examples of these sunscreen agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; U.S. Pat. No. 5,160,731, to Sabatelli et al., issued Nov. 3, 1992; U.S. Pat. No. 5,138,089, to Sabatelli, issued Aug. 11, 1992; U.S. Pat. No. 5,041,282, to Sabatelli, issued Aug. 20, 1991; U.S. Pat. No. 4,999,186, to Sabatelli et al., issued Mar. 12, 1991; U.S. Pat. No. 4,937,370, to Sabatelli, issued Jun. 26, 1990; and Segarin, et al., at Chapter VIII, pages 189 et seq., of Cosmetics Science and Technology; all of these documents being incorporated herein by reference in their entirety. Preferred among the sunscreen agents are those selected from the group consisting of a 2-ethylhexyl p-methoxycinnamate, octyl salicylate, octocrylene, oxybenzone, 2-ethylhexyl N,N-dimethylaminobenzoate, p-aminobenzoic acid, 2-phenyl-benzimidazole-5-sulfonic acid, homomenthyl salicylate, DEA p-methoxycinnamate, 4,4'-methoxy-t-butyldibenzoylmethane, 4-isopropyldibenzoylmethane, 3-(4-methylbenzylidene) camphor, 3-benzylidene camphor, 4-N,N-dimethylaminobenzoic acid ester with 2,4-dihydroxybenzophenone, 4-N,N-dimethylaminobenzoic acid ester with 2-hydroxy-4-(2-hydroxyethoxy)benzophenone, 4-N,N-dimethylaminobenzoic acid ester with 4-hydroxydibenzoyl-methane, 4-N,N-dimethylaminobenzoic acid ester with 4-(2-hydroxyethoxy)dibenzoylmethane, 4-N,N-di(2-ethylhexyl)-aminobenzoic acid ester with 2,4-dihydroxybenzophenone, 4-N,N-di(2-ethylhexyl)aminobenzoic acid ester with 2-hydroxy-4-(2-hydroxyethoxy)benzophenone, 4-N,N-di(2-ethylhexyl)aminobenzoic acid ester with 4-hydroxydibenzoylmethane, 4-N,N-di(2-ethylhexyl)aminobenzoic acid ester with 4-(2-hydroxyethoxy)dibenzoylmethane, 4-N,N-(2-ethylhexyl)methylaminobenzoic acid ester with 2,4-dihydroxybenzophenone, 4-N,N-(2-ethylhexyl)methylaminobenzoic acid ester with 2-hydroxy-4-(2-hydroxyethoxy)benzophenone, 4-N,N-(2-ethylhexyl)methylaminobenzoic acid ester with 4-hydroxydibenzoylmethane, 4-N,N-(2-ethylhexyl)methylaminobenzoic acid ester with 4-(2-hydroxyethoxy)dibenzoylmethane, titanium dioxide, iron oxide, zinc oxide, and mixtures thereof.

More preferred for use in the compositions described herein are the sunscreen agents selected from the group consisting of 2-ethylhexyl N,N-dimethyl-p-aminobenzoate, 2-ethylhexyl p-methoxycinnamate, octocrylene, octyl salicylate, homomenthyl salicylate, p-aminobenzoic acid, oxybenzone, 2-phenylbenzimidazole-5-sulfonic acid, DEA p-methoxycinnamate, 4,4'-methoxy-t-butyldibenzoylmethane, 4-isopropyl dibenzoylmethane, 3-(4-methylbenzylidene) camphor, 3-benzylidene camphor, 4-N,N-(2-ethylhexyl)methylaminobenzoic acid ester with 4-(2-hydroxyethoxy)dibenzoylmethane, titanium dioxide, iron oxide, zinc oxide, and mixtures thereof.

Most preferred for use in the compositions described herein are the sunscreen agents selected from the group consisting of 2-ethylhexyl N,N-dimethyl-p-aminobenzoate, 2-ethylhexyl p-methoxycinnamate, octocrylene, octyl salicylate, oxybenzone, 2-phenylbenzimidazole-5-sulfonic acid, 4,4'-methoxy-t-butyldibenzoylmethane, 3-(4-methylbenzylidene) camphor, 3-benzylidene camphor, 4-N,N-(2-ethylhexyl)methylaminobenzoic acid ester with 4-(2-hydroxyethoxy)dibenzoylmethane, titanium dioxide, iron oxide, zinc oxide, and mixtures thereof.

Humectants and Moisturizers

The compositions of the present invention can also contain one or more humectants or moisturizers. A variety of these materials can be employed and each can be present at a level of from about 0.1% to about 20%, more preferably from about 0.5% to about 10%, and most preferably from about 1% to about 5%. These materials include guanidine; glycolic acid and glycolate salts (e.g., ammonium and quaternary alkyl ammonium); lactic acid and lactate salts (e.g., amnmonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof.

Also, useful are propoxylated glycerols as described in U.S. Pat. No. 4,976,953, to Orr et al., issued Dec. 11, 1990, which is incorporated by reference herein in its entirety. An especially preferred material for use herein is glycerol.

Methods of Personal Cleansing

The compositions of the present invention are useful for personal cleansing, especially for cleansing of the face and neck areas. Typically, a suitable or effective amount of the cleansing composition is applied to the area to be cleansed. Alternatively, a suitable amount of the cleansing composition can be applied via intermediate application to a washcloth, sponge, pad, cotton ball or other application device. If desired, the area to be cleansed can be premoistened with water. It has been found that the compositions of the present invention can be combined with water during the cleansing process and rinsed-off from the skin. Alternatively, the product can be used alone and wiped-off from the skin using a pad, cotton ball, tissue, or other like device. The cleansing process is typically a two-step process involving application of the product followed either by rinsing of the product with water or wiping without the use of water. Generally, an effective amount of product to be used will depend upon the needs and usage habits of the individual. Typical amounts of the present compositions useful for cleansing range from about 0.5 mg/cm$^2$ to about 25 mg/cm$^2$ of skin area to be cleansed.

EXAMPLES

The following examples further described and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

EXAMPLES

Example 1

A personal cleanser composition is prepared by combining the following ingredients using conventional mixing techniques.

| Ingredients | Weight Percent |
| --- | --- |
| Phase A | |
| Water | QS 100 |
| Disodium EDTA | 0.100 |
| Glycerin | 4.00 |
| Methylparaben | 0.200 |
| Acrylates/C10–30 alkyl acrylate Crosspolymer[1] | 0.150 |
| Carbomer 954[2] | 0.250 |
| Phase B | |
| Stearic Acid | 0.110 |
| Stearyl Alcohol | 0.875 |
| Cetyl Alcohol | 0.875 |

| Ingredients | Weight Percent |
| --- | --- |
| Propylparaben | 0.150 |
| Phase C | |
| Sodium Hydroxide[3] | 0.130 |
| Phase D | |
| Diisopropyl sebacate | 1.50 |
| Isohexadecane | 5.00 |
| Phase E | |
| Phenoxyethanol | 0.50 |
| Fragrance | 0.150 |
| Phase F | |
| Glucose Amide | 0.96 |

[1]Available as Pemulen ® TR-1 from B. F. Goodrich Corporation.
[2]Available as Carbomer ® 954 from B. F. Goodrich Corporation.
[3]50% aqueous solution.

In a suitable vessel, the Phase A ingredients are mixed at room temperature to form a dispersion and heated with stirring to 70°–80° C. In a separate vessel, the Phase B ingredients are heated with stirring to 70°–80° C. Phase B is then added to Phase A with mixing to form the emulsion. Next, Phase C is added to neutralize the composition. The Phase D ingredients are added with mixing, followed by cooling to 45°–50° C. The Phase E ingredients are then added with stirring, followed by cooling to 40° C. Phase F is heated with mixing to 40° C. and added to the emulsion, which is cooled to room temperature.

The resulting cleansing composition is useful for cleansing the skin. The emulsion de-emulsifies upon contact with the skin.

Alternatively, an extra-conditioning cleanser is prepared by increasing the glycerin to 7% and making a corresponding decrease in the water level.

In another alternative, the isohexadecane is replaced with an equal weight of isododecane.

Example 2

A personal cleanser composition is prepared by combining the following ingredients using conventional mixing techniques.

| Ingredients | Weight Percent |
| --- | --- |
| Phase A | |
| Water | QS 100 |
| Disodium EDTA | 0.100 |
| Glycerin | 4.00 |
| Methylparaben | 0.200 |
| Acrylates/C10–30 alkyl acrylate Crosspolymer[1] | 0.150 |
| Carbomer 954[2] | 0.250 |
| Phase B | |
| Stearic Acid | 0.110 |
| Stearyl Alcohol | 0.875 |
| Cetyl Alcohol | 0.875 |
| Propylparaben | 0.150 |
| Steareth-2 | 0.25 |
| Steareth-21 | 0.50 |
| Phase C | |
| Sodium Hydroxide[3] | 0.130 |
| Phase D | |
| Diisopropyl sebacate | 1.50 |
| Isohexadecane | 2.00 |
| Mineral Oil[4] | 5.00 |

| Ingredients | Weight Percent |
| --- | --- |
| Phase E | |
| Phenoxyethanol | 0.50 |
| Fragrance | 0.150 |
| Phase F | |
| Glucose Amide | 0.96 |

[1]Available as Pemulen ® TR-1 from B. F. Goodrich Corporation.
[2]Available as Carbomer ® 954 from B. F. Goodrich Corporation.
[3]50% aqueous solution.
[4]Light mineral oil available as Drakeol 5 from Penreco, Dickenson, TX).

In a suitable vessel, the Phase A ingredients are mixed at room temperature to form a dispersion and heated with stirring to 70°–80° C. In a separate vessel, the Phase B ingredients are heated with stirring to 70°–80° C. Phase B is then added to Phase A with mixing to form the emulsion. Next, Phase C is added to neutralize the composition. The Phase D ingredients are added with mixing, followed by cooling to 45°–50° C. The Phase E ingredients are then added with stirring, followed by cooling to 40° C. Phase F is heated with mixing to 40° C. and added to the emulsion, which is cooled to room temperature.

The resulting cleansing composition is useful for cleansing the skin. The emulsion de-emulsifies upon contact with the skin.

Alternatively, an extra-conditioning cleanser is prepared by increasing the glycerin to 7% and making a corresponding decrease in the water level.

In another alternative, the isohexadecane is replaced with an equal weight of isododecane.

Example 3

A personal cleanser composition is prepared by combining the following ingredients using conventional mixing techniques.

| Ingredients | Weight Percent |
| --- | --- |
| Phase A | |
| Water | QS 100 |
| Disodium EDTA | 0.100 |
| Glycerin | 4.00 |
| Methylparaben | 0.200 |
| Acrylates/C10–30 alkyl acrylate Crosspolymer[1] | 0.150 |
| Carbomer 954[2] | 0.250 |
| Phase B | |
| Stearic Acid | 0.110 |
| Stearyl Alcohol | 0.875 |
| Cetyl Alcohol | 0.875 |
| Propylparaben | 0.150 |
| Steareth-2 | 0.25 |
| Steareth-21 | 0.50 |
| Phase C | |
| Sodium Hydroxide[3] | 0.130 |
| Phase D | |
| Diisopropyl sebacate | 1.50 |
| Isohexadecane | 5.00 |
| Phase E | |
| Phenoxyethanol | 0.50 |
| Fragrance | 0.150 |
| Phase F | |
| Glucose Amide | 0.96 |

[1]Available as Pemulen ® TR-1 from B. F. Goodrich Corporation.
[2]Available as Carbomer ® 954 from B. F. Goodrich Corporation.
[3]50% aqueous solution.

In a suitable vessel, the Phase A ingredients are mixed at room temperature to form a dispersion and heated with stirring to 70°–80° C. In a separate vessel, the Phase B ingredients are heated with stirring to 70°–80° C. Phase B is then added to Phase A with mixing to form the emulsion. Next, Phase C is added to neutralize the composition. The Phase D ingredients are added with mixing, followed by cooling to 45°–50° C. The Phase E ingredients are then added with stirring, followed by cooling to 40° C. Phase F is heated with mixing to 40° C. and added to the emulsion, which is cooled to room temperature.

The resulting cleansing composition is useful for cleansing the skin. The emulsion de-emulsifies upon contact with the skin.

Alternatively, an extra-conditioning cleanser is prepared by increasing the glycerin to 7% and making a corresponding decrease in the water level.

In another alternative, the isohexadecane is replaced with an equal weight of isododecane.

Example 4

A personal cleanser composition is prepared by combining the following ingredients using conventional mixing techniques.

| Ingredients | Weight Percent |
| --- | --- |
| Phase A | |
| Water | QS 100 |
| Disodium EDTA | 0.100 |
| Glycerin | 4.00 |
| Methylparaben | 0.200 |
| Acrylates/C10–30 alkyl acrylate Crosspolymer[1] | 0.150 |
| Carbomer 954[2] | 0.250 |
| Phase B | |
| Stearic Acid | 0.110 |
| Stearyl Alcohol | 0.875 |
| Cetyl Alcohol | 0.875 |
| Propylparaben | 0.150 |
| Steareth-2 | 0.10 |
| Steareth-21 | 0.10 |
| Phase C | |
| Sodium Hydroxide[3] | 0.130 |
| Phase D | |
| Diisopropyl sebacate | 1.50 |
| Isohexadecane | 5.00 |
| Phase E | |
| Phenoxyethanol | 0.50 |
| Fragrance | 0.150 |
| Phase F | |
| Glucose Amide | 0.96 |

[1]Available as Pemulen ® TR-1 from B. F. Goodrich Corporation.
[2]Available as Carbomer ® 954 from B. F. Goodrich Corporation.
[3]50% aqueous solution.

In a suitable vessel, the Phase A ingredients are mixed at room temperature to form a dispersion and heated with stirring to 70°–80° C. In a separate vessel, the Phase B ingredients are heated with stirring to 70°–80° C. Phase B is then added to Phase A with mixing to form the emulsion.

Next, Phase C is added to neutralize the composition. The Phase D ingredients are added with mixing, followed by cooling to 45°–50° C. The Phase E ingredients are then added with stirring, followed by cooling to 40° C. Phase F is heated with mixing to 40° C. and added to the emulsion, which is cooled to room temperature.

The resulting cleansing composition is useful for cleansing the skin. The emulsion de-emulsifies upon contact with the skin.

Example 5

A personal cleanser composition is prepared by combining the following ingredients using conventional mixing techniques.

| Ingredients | Weight Percent |
| --- | --- |
| Phase A | |
| Water | QS 100 |
| Disodium EDTA | 0.100 |
| Glycerin | 4.00 |
| Methylparaben | 0.200 |
| Acrylates/C10–30 alkyl acrylate Crosspolymer[1] | 0.150 |
| Carbomer 954[2] | 0.250 |
| Phase B | |
| Stearic Acid | 0.110 |
| Stearyl Alcohol | 0.875 |
| Cetyl Alcohol | 0.875 |
| Propylparaben | 0.150 |
| Steareth-2 | 0.25 |
| Steareth-21 | 0.50 |
| Phase C | |
| Sodium Hydroxide[3] | 0.130 |
| Phase D | |
| Diisopropyl sebacate | 1.50 |
| Isohexadecane | 5.00 |
| Phase E | |
| Phenoxyethanol | 0.50 |
| Fragrance | 0.150 |
| Phase F | |
| Decyl Polyglucose[4] | 0.96 |
| Lauric Acid | 0.10 |

[1]Available as Pemulen ® TR-1 from B. F. Goodrich Corporation.
[2]Available as Carbomer ® 954 from B. F. Goodrich Corporation.
[3]50% aqueous solution.
[4]Available as Plantaren ® from Henkel Corp.

In a suitable vessel, the Phase A ingredients are mixed at room temperature to form a dispersion and heated with stirring to 70°–80° C. In a separate vessel, the Phase B ingredients are heated with stirring to 70°–80° C. Phase B is then added to Phase A with mixing to form the emulsion. Next, Phase C is added to neutralize the composition. The Phase D ingredients are added with mixing, followed by cooling to 45°–50° C. The Phase E ingredients are then added with stirring, followed by cooling to 40° C. Phase F is heated with mixing to 40° C. and added to the emulsion, which is cooled to room temperature.

The resulting cleansing composition is useful for cleansing the skin. The emulsion de-emulsifies upon contact with the skin.

Example 6

A personal cleanser composition is prepared by combining the following ingredients using conventional mixing techniques.

| Ingredients | Weight Percent |
| --- | --- |
| Phase A | |
| Water | QS 100 |
| Disodium EDTA | 0.100 |
| Glycerin | 4.00 |
| Methylparaben | 0.200 |
| Acrylates/C10–30 alkyl acrylate Crosspolymer[1] | 0.150 |
| Carbomer 954[2] | 0.250 |
| Phase B | |
| Stearic Acid | 0.110 |
| Stearyl Alcohol | 0.875 |
| Cetyl Alcohol | 0.875 |
| Propylparaben | 0.150 |
| Steareth-2 | 0.25 |
| Steareth-21 | 0.50 |
| Phase C | |
| Sodium Hydroxide[3] | 0.130 |
| Phase D | |
| Dioctyl Maleate | 1.50 |
| Isohexadecane | 5.00 |
| Phase E | |
| Phenoxyethanol | 0.50 |
| Fragrance | 0.150 |
| Phase F | |
| Glucose Amide | 0.96 |

[1]Available as Pemulen ® TR-1 from B. F. Goodrich Corporation.
[2]Available as Carbomer ® 954 from B. F. Goodrich Corporation.
[3]50% aqueous solution.

In a suitable vessel, the Phase A ingredients are mixed at room temperature to form a dispersion and heated with stirring to 70°–80° C. In a separate vessel, the Phase B ingredients are heated with stirring to 70°–80° C. Phase B is then added to Phase A with mixing to form the emulsion. Next, Phase C is added to neutralize the composition. The Phase D ingredients are added with mixing, followed by cooling to 45°–50° C. The Phase E ingredients are then added with stirring, followed by cooling to 40° C. Phase F is heated with mixing to 40° C. and added to the emulsion, which is cooled to room temperature.

The resulting cleansing composition is useful for cleansing the skin. The emulsion de-emulsifies upon contact with the skin.

Example 7

A personal cleanser composition is prepared by combining the following ingredients using conventional mixing techniques. This composition utilizes a mixture of silicone materials to provide improved skin feel.

| Ingredients | Weight Percent |
| --- | --- |
| Phase A | |
| Water | QS 100 |
| Disodium EDTA | 0.100 |
| Glycerin | 4.00 |
| Methylparaben | 0.200 |
| Acrylates/C10–30 alkyl acrylate Crosspolymer[1] | 0.150 |
| Carbomer 954[2] | 0.250 |
| Phase B | |
| Stearic Acid | 0.110 |
| Stearyl Alcohol | 0.875 |
| Cetyl Alcohol | 0.875 |
| Propylparaben | 0.150 |

| Ingredients | Weight Percent |
| --- | --- |
| Steareth-2 | 0.25 |
| Steareth-21 | 0.50 |
| Phase C | |
| Sodium Hydroxide[3] | 0.130 |
| Phase D | |
| Diisopropyl sebacate | 1.50 |
| Isohexadecane | 5.00 |
| Phase E | |
| Phenoxyethanol | 0.50 |
| Fragrance | 0.150 |
| Phase F | |
| Glucose Amide | 0.96 |
| Phase G | |
| Cyclomethicone[4] | 1.22 |
| Cyclomethicone and Dimethiconol[5] | 0.58 |
| Cyclomethicone and Dimethiconecopolyol[6] | 0.58 |
| Dimethiconecopolyol[7] | 0.12 |

[1] Available as Pemulen® TR-1 from B. F. Goodrich Corporation.
[2] Available as Carbomer® 954 from B. F. Goodrich Corporation.
[3] 50% aqueous solution.
[4] Available as Dow Corning 245 fluid.
[5] Available as Dow Corning 1401 fluid.
[6] Available as Dow Corning 3225C fluid.
[7] Available as Dow Corning 193 fluid.

In a suitable vessel, the Phase A ingredients are mixed at room temperature to form a dispersion and heated with stirring to 70°–80° C. In a separate vessel, the Phase B ingredients are heated with stirring to 70°–80° C. Phase B is then added to Phase A with mixing to form the emulsion. Next, Phase C is added to neutralize the composition. The Phase D ingredients are added with mixing, followed by cooling to 45°–50° C. The Phase E ingredients are then added with stirring, followed by cooling to 40° C. Phase F is heated with mixing to 40° C. and added to the emulsion. Next Phase G is combined with stirring and added to the emulsion which is then cooled to room temperature.

The resulting cleansing composition is useful for cleansing the skin. The emulsion de-emulsifies upon contact with the skin.

Example 8

A personal cleanser composition is prepared by combining the following ingredients using conventional mixing techniques. This composition utilizes a mixture of sucrose polyesters to provide improved skin feel and moisturization.

| Ingredients | Weight Percent |
| --- | --- |
| Phase A | |
| Water | QS 100 |
| Disodium EDTA | 0.100 |
| Glycerin | 4.00 |
| Methylparaben | 0.200 |
| Acrylates/C10-30 alkyl acrylate Crosspolymer[1] | 0.150 |
| Carbomer 954[2] | 0.250 |
| Phase B | |
| Stearic Acid | 0.110 |
| Stearyl Alcohol | 0.875 |
| Cetyl Alcohol | 0.875 |
| Propylparaben | 0.150 |
| Steareth-2 | 0.25 |
| Steareth-21 | 0.50 |
| Liquid Sucrose Polyester[3] | 2.78 |

| Ingredients | Weight Percent |
| --- | --- |
| Solid Sucrose Polyester[4] | 0.22 |
| Phase C | |
| Sodium Hydroxide[5] | 0.130 |
| Phase D | |
| Diisopropyl sebacate | 1.50 |
| Isohexadecane | 5.00 |
| Phase E | |
| Phenoxyethanol | 0.50 |
| Fragrance | 0.150 |
| Phase F | |
| Glucose Amide | 0.96 |

[1] Available as Pemulen® TR-1 from B. F. Goodrich Corporation.
[2] Available as Carbomer® 954 from B. F. Goodrich Corporation.
[3] Liquid mixed hexa-, hepta, and octa-sucrose esters, predominately the octa-ester esterified with mixed soybean oil fatty acids.
[4] Solid sucrose octaester esterified with 1 oleic acid and 7 behenic acid moieties.
[5] 50% aqueous solution.

In a suitable vessel, the Phase A ingredients are mixed at room temperature to form a dispersion and heated with stirring to 70°–80° C. In a separate vessel, the Phase B ingredients are heated with stirring to 70°–80° C. Phase B is then added to Phase A with mixing to form the emulsion. Next, Phase C is added to neutralize the composition. The Phase D ingredients are added with mixing, followed by cooling to 45°–50° C. The Phase E ingredients are then added with stirring, followed by cooling to 40° C. Phase F is heated with mixing to 40° C. and added to the emulsion, which is cooled to room temperature.

The resulting cleansing composition is useful for cleansing the skin. The emulsion de-emulsifies upon contact with the skin.

Example 9

The following emulsion forming experiment was conducted using a model system of water and 10 parts by weight mineral oil.

Eight samples were prepared having the indicated compositions:

Beaker 1: 10 parts by weight mineral oil[1] and 90 parts by weight of water.
[1] Light mineral oil available as Drakeol 5 from Penreco, Dickenson, Tex.

Beaker 2: 10 parts by weight mineral oil[1], 88 parts by weight of water, and 2 parts by weight of glucose amide.
[1] Light mineral oil available as Drakeol 5 from Penreco, Dickenson, Tex.

Beaker 3: 10 parts by weight mineral oil[1], 88 parts by weight of water, and 2 parts by weight of decyl polyglucose.
[1] Light mineral oil available as Drakeol 5 from Penreco, Dickenson, Tex.

Beaker 4: 10 parts by weight mineral oil[1], 88 parts by weight of water, 1 part by weight of steareth-2, and 1 part by weight of steareth-21.
[1] Light mineral oil available as Drakeol 5 from Penreco, Dickenson, Tex.

Beaker 5: 10 parts by weight mineral oil[1], 89.735 parts by weight of water, 0.2 parts by weight of acrylates/C10–30 alkylate crosspolymer[2], and 0.065 parts by weight of 50% sodium hydroxide aqueous solution.
[1] Light mineral oil available as Drakeol 5 from Penreco, Dickenson, Tex.
[2] Available as Pemulen® TR-1 from B. F. Goodrich Corporation.

Beaker 6: 10 parts by weight mineral oil[1], 87.735 parts by weight of water, 0.2 parts by weight of acrylates/C10–30 alkyl acrylate crosspolymer[1], and 0.065 parts by weight of 50% sodium hydroxide aqueous solution, and 2 parts by weight glucose amide.

[1]Light mineral oil available as Drakeol 5 from Penreco, Dickenson, Tex.

Beaker 7: 10 parts by weight mineral oil[1], 87.735 parts by weight of water, 0.2 parts by weight of acrylates/C10–30 alkyl acrylate crosspolymer[1], and 0.065 parts by weight of 50% sodium hydroxide aqueous solution, and 2 parts by weight decyl polyglucose.

[1]Light mineral oil available as Drakeol 5 from Penreco, Dickenson, Tex.

Beaker 8: 10 parts by weight mineral oil[1], 87.735 parts by weight of water, 0.2 parts by weight of acrylates/C10–30 alkyl acrylate crosspolymer[1], and 0.065 parts by weight of 50% sodium hydroxide aqueous solution, 1 part by weight of steareth-2, and 1 part by weight of steareth-21.

[1]Light mineral oil available as Drakeol 5 from Penreco, Dickenson, Tex.

The contents of Beaker 1 was vigorously stirred with an overhead mixer for approximately 30 seconds.

For Beakers 2–4, the water and surfactants were combined and heated to 70° C. The mineral oil was separately heated to 70° C. and added to the water phase. The oil and water mixture was vigorously stirred with an overhead mixer for approximately 30 seconds.

For Beakers 5–8, the water, the acrylates/C10–30 alkyl acrylate crosspolymer, and the surfactants (Beakers 6–8) were combined and heated to 70° C. The mineral oil was separately heated to 70° C. and added to the water phase. The oil and water mixture was vigorously stirred with an overhead mixer for approximately 30 seconds. The sodium hydroxide solution was then added with mixing to neutralize the crosspolymer.

After, standing for approximately 6 hours, each beaker was visually inspected to determine whether there were one or two phases present. The presence of one phase would indicate that emulsification had occurred and the presence of two phases would indicate that emulsification had not occurred. The following is a tabulation of the results.

| Beaker | Copolymer | Surfactant | Phases Observed |
| --- | --- | --- | --- |
| 1 | none | none | 2 |
| 2 | none | glucose amide | 2 |
| 3 | none | decyl polyglucose | 2 |
| 4 | none | Steareth-2/Steareth-21 | 1 |
| 5 | Yes | none | 1 |
| 6 | Yes | glucose amide | 1 |
| 7 | Yes | decyl polyglucose | 1 |
| 8 | Yes | Steareth-2/Steareth-21 | 1 |

When neither copolymer nor surfactant are present (Beaker 1) an emulsion is not formed as seen by the presence of 2 phases after mixing. The results from Beakers 2 and 3, i.e. 2 phases remaining after mixing, demonstrate that surfactants such as glucose amide and decyl polygluce are non-emulsifying surfactants. The result from Beaker 4, shows that the 1:1 combination of Steareth-2 and Steareth-21 is an emulsifying surfactant. The acrylates/C10–30 alkyl acrylate crosspolymer, when neutralized with an appropriate base such as sodium hydroxide, acts as an emulsifier when used along (Beaker 5) or in combination with a surfactant system (Beakers 6–8).

These results demonstrate that acrylates/C10–C30 alkyl acrylate crosspolymer can emulsify a simple oil such as mineral oil and that a surfactant can be either an emulsifying or a non-emulsifying surfactant.

What is claimed is:

1. A composition for personal cleansing in the form of an oil-in-water emulsion that is free from polymerized 1-alkenes having 10 or more carbon atoms, said emulsion having the characteristic of de-emulsifying on contact with the human skin, comprising:

(a) from about 0.01% to about 5% by weight of a copolymer comprising a monomer selected from the group consisting of acrylic acid, salts of acrylic acid, C1–C4 alkyl-substituted acrylic acid, salts of C1–C4 alkyl-substituted acrylic acid, C1–C4 alkyl esters of acrylic acid, C1–C4 alkyl esters of C1–C4 alkyl-substituted acrylic acid, maleic anhydride, and mixtures thereof; and a monomer selected from the group consisting of C10–C30 alkyl esters of acrylic acid, C10–C30 alkyl esters of C1–C4 alkyl-substituted acrylic acid, and mixtures thereof, (b) from about 0.05% to about 20% by weight of a nonionic non-emulsifying detersive surfactant having a HLB greater than about 11 corresponding to the chemical formula:

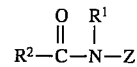

wherein $R^1$ is selected from the group consisting of H, $C_1$–$C_4$ alkyl, 2-hydroxyethyl, or 2-hydroxy-propyl; $R^2$ is selected from the group consisting of $C_5$–$C_{31}$ alkyl or alkenyl; and Z is selected from the group consisting of polyhydroxyhydrocarbyl moieties having a linear hydrocarbyl chain with at least 3 hydroxyls directly connected to the chain, or an alkoxylated derivative thereof, (c) from about 0.5% to about 40% by weight of an oil selected from the group consisting of mineral oil, petrolatum, C7–C40 branched chain hydrocarbons, C1–C30 alcohol esters of C1–C30 carboxylic acids, monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, propylene glycol diesters of C1–C30 carboxylic acids, C1–C30 carboxylic acid sugar esters, C1–C30 carboxylic acid sugar polyesters, polydialkylsiloxanes, polydiaryl siloxanes, polyalkarylsiloxanes, cyclomethicones having 3 to 9 silicon atoms, vegetable oils, hydrogenated vegetable oils, polypropylene glycols, polypropylene glycol C4–C20 alkyl ethers, C1–C20 carboxylic acid esters of polypropylene glycols, di C8–C30 alkyl ethers, and mixtures thereof, and (d) from about 20% to about 99.44% by weight water.

2. A composition according to claim 1 wherein said copolymer further comprises a crosslinking agent.

3. A composition according to claim 2 wherein said crosslinking agent is a polyalkenyl polyether of a polyhydric alcohol containing at least 3 carbon atoms and at least three hydroxy groups.

4. A composition according to claim 3 wherein said crosslinking agent is selected from the group consisting of allyl ethers of sucrose, allyl ethers of pentaerythritol, and mixtures thereof.

5. A composition according to claim 4 wherein said copolymer is an acrylates/C10–30 alkyl acrylate crosspolymer.

6. A composition according to claim 5 wherein said oil is selected from the group consisting of mineral oil, petrolatum, and mixtures thereof.

7. A composition according to claim 5 wherein said oil is selected from the group consisting of polydialkylsiloxanes, cyclomethicones having 3 to 9 silicon atoms, and mixtures thereof.

8. A composition according to claim 5 wherein said oil is selected from the group consisting of vegetable oils, hydrogenated vegetable oils, and mixtures thereof.

9. A composition according to claim 5 wherein said oil is selected from the group consisting of C1–C30 alcohol esters of C1–C30 carboxylic acids, monoglycerides of C1–C30 alcohols, diglycerides of C1–C30 alcohols, triglycerides of C1–C30 alcohols, ethylene glycol monoesters of C1–C30 carboxylic acids, ethylene glycol diesters of C1–C30 carboxylic acids, propylene glycol monoesters of C1–C30 carboxylic acids, propylene glycol diesters of C1–C30 carboxylic acids, and mixtures thereof.

10. A composition according to claim 5 wherein said oil is selected from the group consisting of C7–C40 straight and branched chain hydrocarbons, and mixtures thereof.

11. A composition according to claim 5 wherein said oil is selected from the group consisting of isododecane, isohexadecane, and mixtures thereof.

12. A composition according to claim 1 wherein said emulsion is in the form of a rinse-off composition.

13. A composition according to claim 1 wherein said emulsion is in the form of a wipe-off composition.

14. A method for cleansing skin comprising the steps of
(1) applying to the skin from about 0.5 mg/cm$^2$ to about 25 mg/cm$^2$ of the composition of claim 1, and
(2) rinsing the composition of claim 1 from the skin.

15. A method for cleansing skin comprising the steps of:
(1) applying to the skin from about 0.5 mg/cm$^2$ to about 25 mg/cm$^2$ of the composition of claim 1, and
(2) wiping the composition of claim 1 from the skin.

* * * * *

UNITED STATES PATENT AND TRADEMARK OFFICE
CERTIFICATE OF CORRECTION

PATENT NO. : 5,585,104

DATED : December 17, 1996

INVENTOR(S) : Robert B. K. Ha, Timothy J. Fowler, George E. Deckner

It is certified that error appears in the above-indentified patent and that said Letters Patent is hereby corrected as shown below:

At Column 1, line 41 "storage ability" should read --storage stability--.

At Column 2, line 42 "thereof." should read --thereof,--.

At Column 3, line 38 "compositions" should read --composition--.

At Column 5, line 47 "carboxyloxyethylene" should read --carbonyloxyethylene--.

At Column 5, line 57 "measured to" should read --measured at--.

At Column 7, line 19 "re-dox" should read --redox--.

At Column 10, line 33 "caster" should read --castor--.

At Column 10, line 57 "toms" should read --atoms--.

At Column 11, line 42 "quarternary" should read --quaternary--.

At Column 12, line 25 "is entirety" should read --its entirety--.

At Column 12, line 63-64 "monoethanoamide" should read --monoethanolamide--.

At Column 13, line 45 "Inc." should read --Ind.--.

At Column 13, line 59 "C1-C 30" should read --C1-C30--.

At Column 15, line 32 "and Dow" should read --Dow--.

At Column 16, line 62 "CFTA" should read --CTFA--.

At Column 17, line 2 "polyethylene glycols" should read --polyethyleneglycols--.

At Column 17, line 8 "salicyclic" should read --salicylic--.

At Column 18, line 7 "consisting of a" should read --consisting of--.

UNITED STATES PATENT AND TRADEMARK OFFICE
CERTIFICATE OF CORRECTION

PATENT NO. : 5,585,104
DATED : December 17, 1996
INVENTOR(S) : Robert B. K. Ha, Timothy J. Fowler, George E. Deckner It is certified that error appears in the above-indentified patent and that said Letters Patent is hereby corrected as shown below:

At Column 18, line 67 "amnmonium" should read --ammonium--.

At Column 19, line 38 "described" should read --describe--.

At Column 26, line 10 "Isohexadecalic" should read --Isohexadecane--.

At Column 26, line 59 "alkylate" should read --alkyl acrylate--.

At Column 27, line 54 "along" should read --alone--.

Signed and Sealed this

Sixth Day of May, 1997

Attest:

BRUCE LEHMAN

Attesting Officer

Commissioner of Patents and Trademarks